United States Patent [19]

Larkin

[11] 4,246,903
[45] Jan. 27, 1981

[54] SURGICAL INSTRUMENT TO APPLY A HEMOSTATIC CLIP TO A VESSEL AND METHOD OF USING THE SAME

[75] Inventor: Joseph F. Larkin, Holland, Pa.

[73] Assignee: American Cyanamid Company, Stamford, Conn.

[21] Appl. No.: 26,614

[22] Filed: Apr. 2, 1979

[51] Int. Cl.³ .............................................. A61B 17/12
[52] U.S. Cl. .................................... 128/325; 29/243.56
[58] Field of Search .................. 128/325, 321, 334 R, 128/337, 335; 29/243.56; 72/410; 227/DIG. 1

[56] References Cited

U.S. PATENT DOCUMENTS

| | | | |
|---|---|---|---|
| 2,968,041 | 1/1961 | Skold | 128/335 |
| 3,234,636 | 2/1966 | Brown | 128/334 R |
| 3,266,494 | 8/1966 | Brownrigg et al. | 128/321 |
| 4,152,920 | 5/1979 | Green | 29/243.56 X |
| 4,166,466 | 9/1979 | Jarvik | 128/325 |

FOREIGN PATENT DOCUMENTS 2347418  4/1974  Fed. Rep. of Germany ...... 128/334 R

Primary Examiner—Robert W. Michell
Assistant Examiner—Michael H. Thaler
Attorney, Agent, or Firm—Jack W. Richards

[57] ABSTRACT

The surgical instrument comprises a single housing having a barrel and handle. The barrel contains jaws to maintain a hemostatic clip, and a jaw wedge. When actuated by the jaw wedge, the jaws operate in a "scissors action" to compress the hemostatic clip onto the vessel.

The barrel portion also contains a feed bar and magazine tape. The magazine tape contains a plurality of hemostatic clips. On retraction, the jaw wedge coordinates with the feed bar and magazine tape to deliver a new clip to the jaws.

The jaw wedge is actuated by a trigger pivotally mounted to the handle.

11 Claims, 14 Drawing Figures

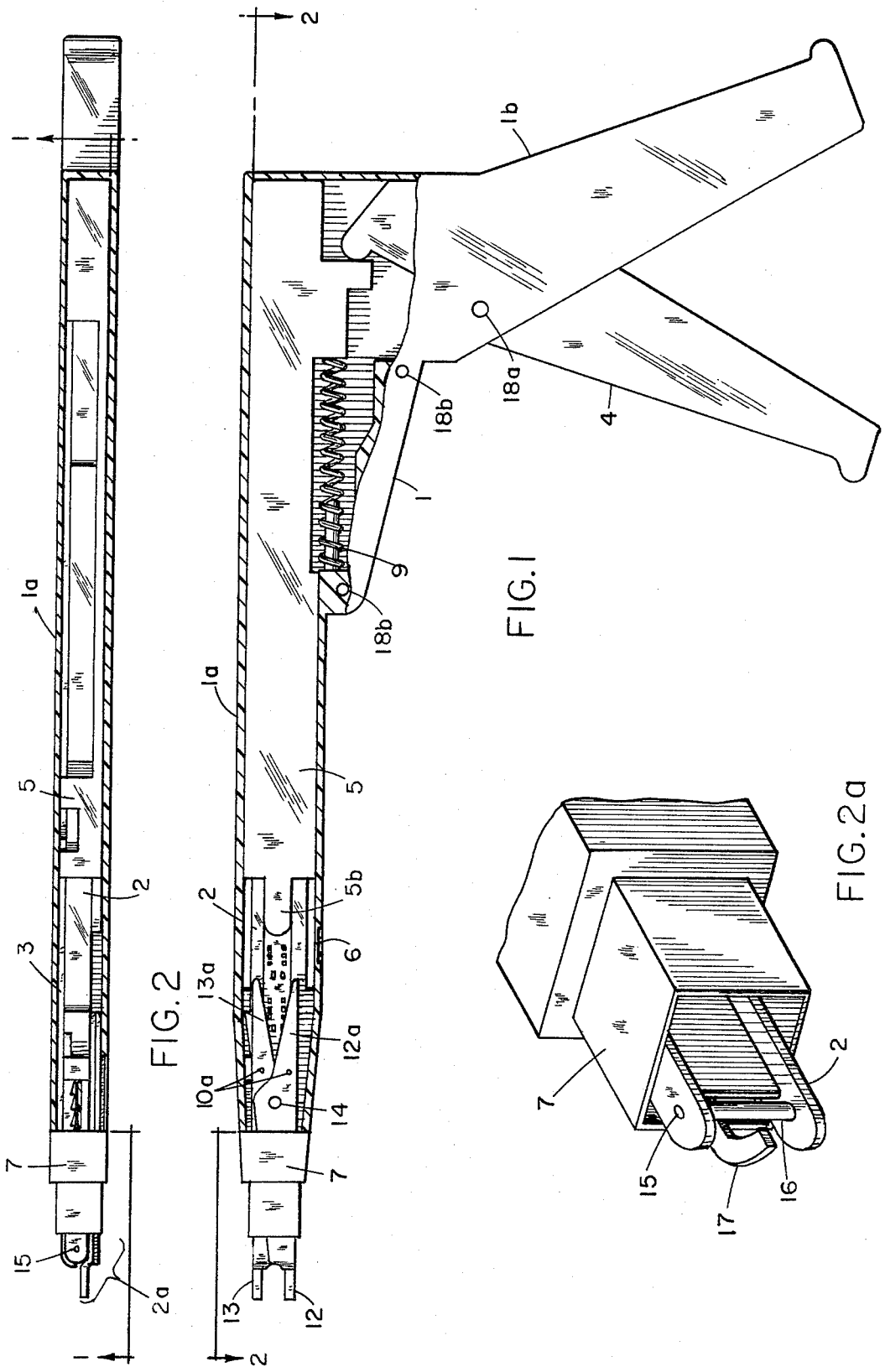

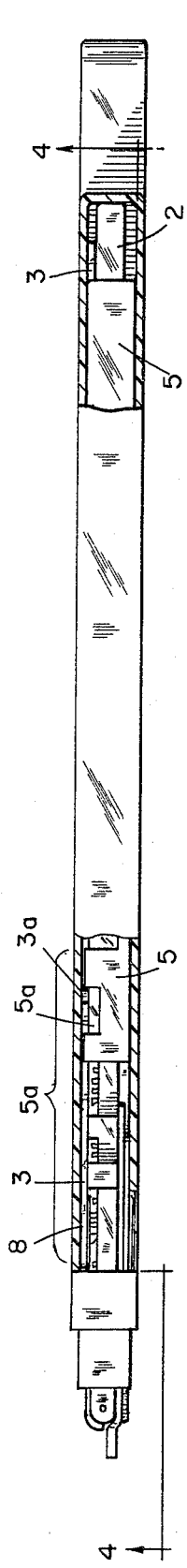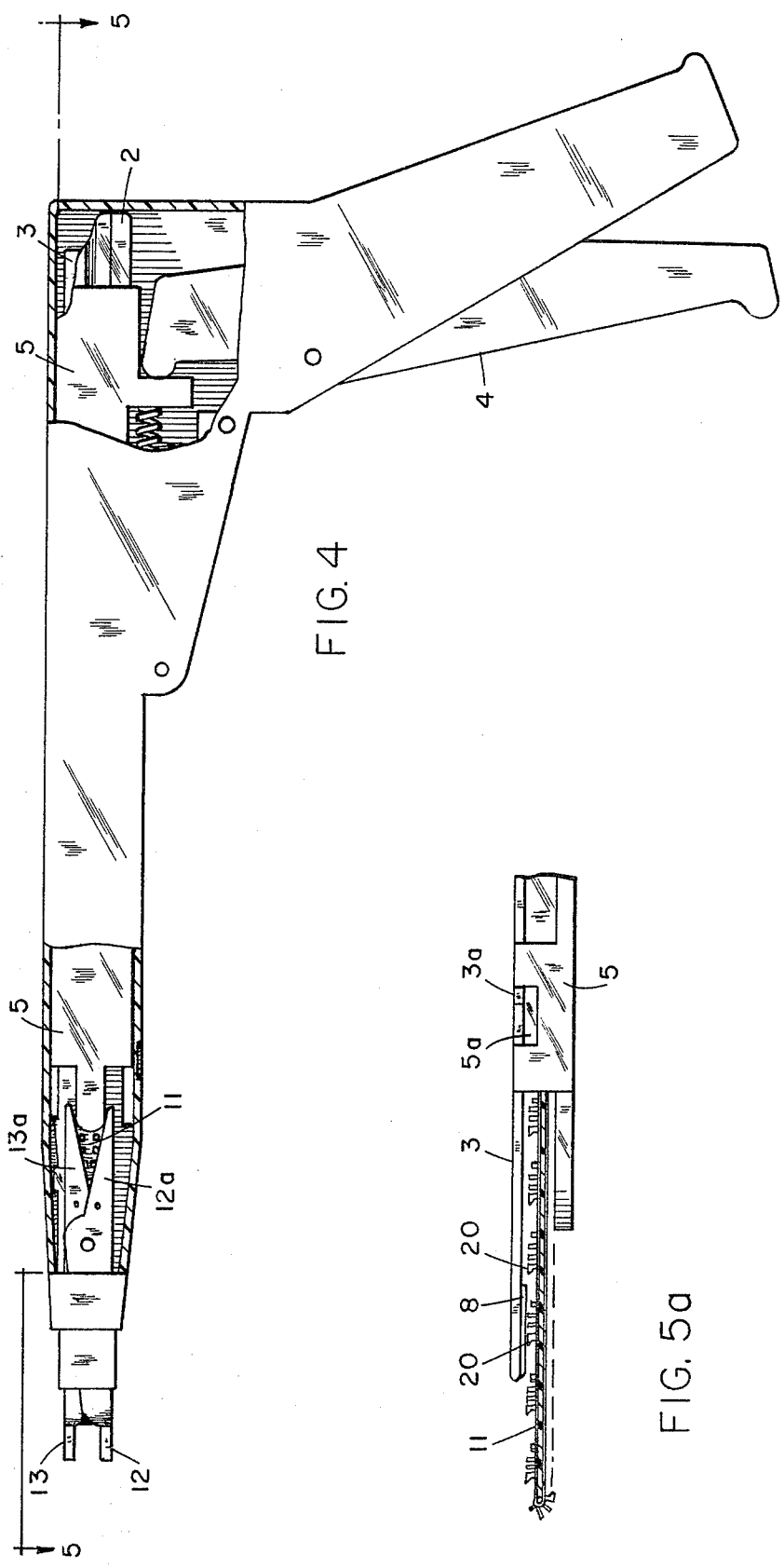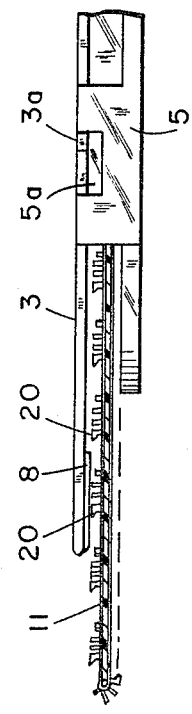
FIG. 4
FIG. 5
FIG. 5a

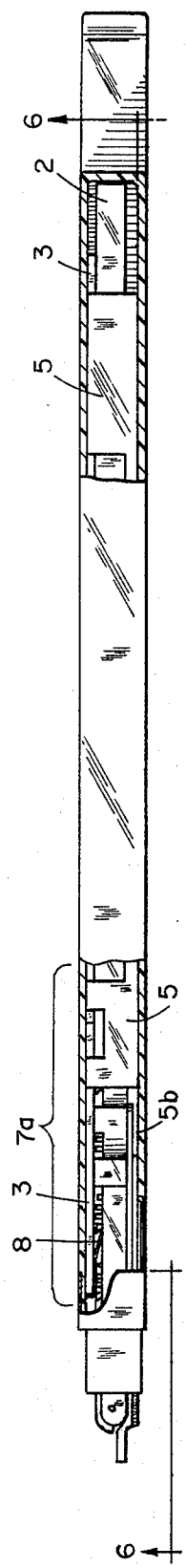
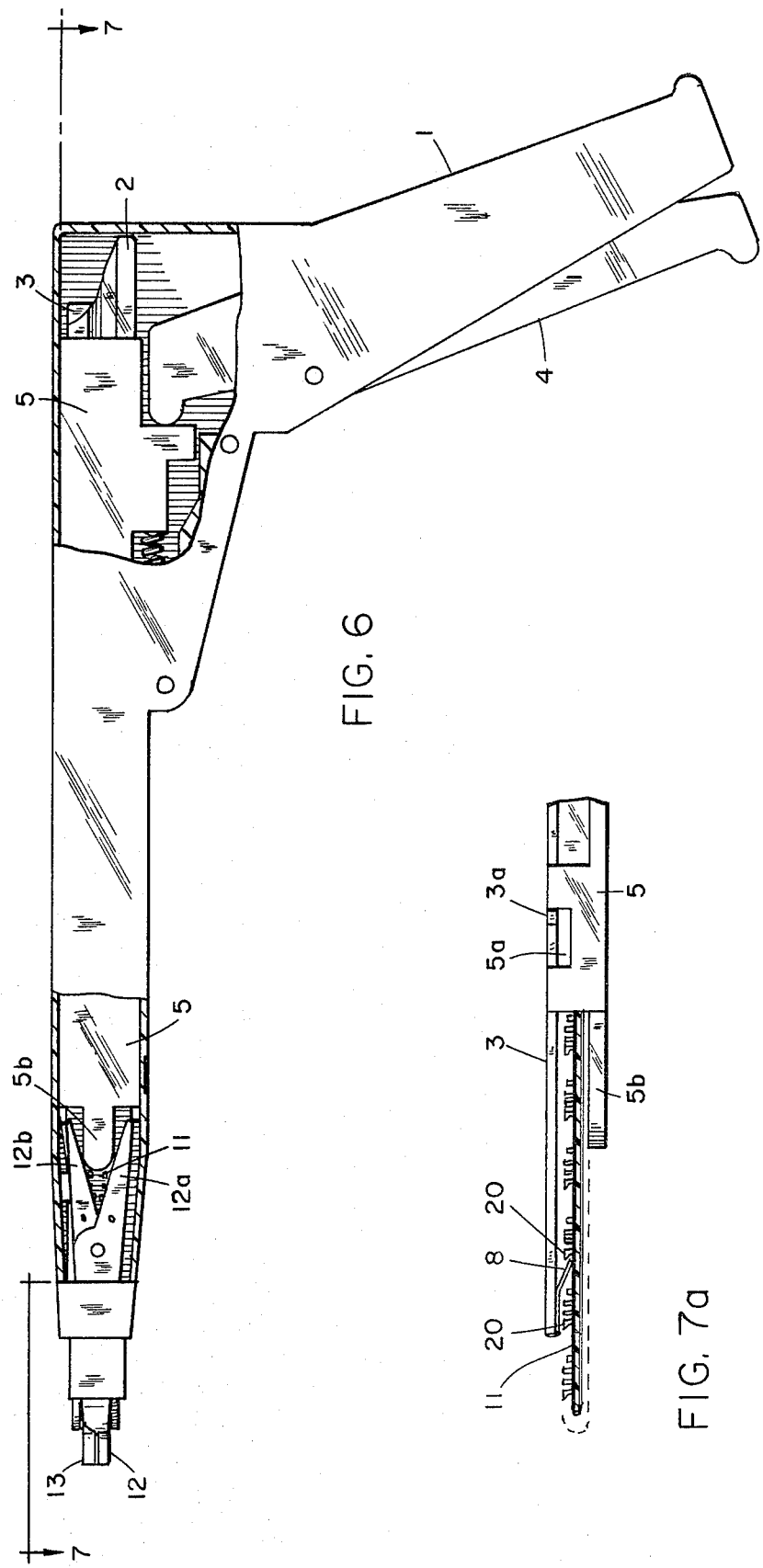
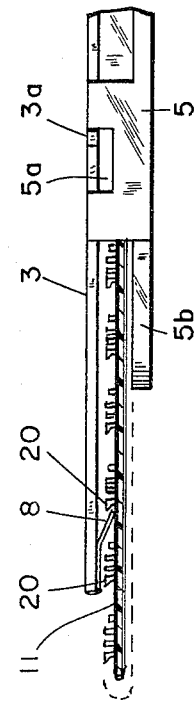
FIG. 6
FIG. 7
FIG. 7a

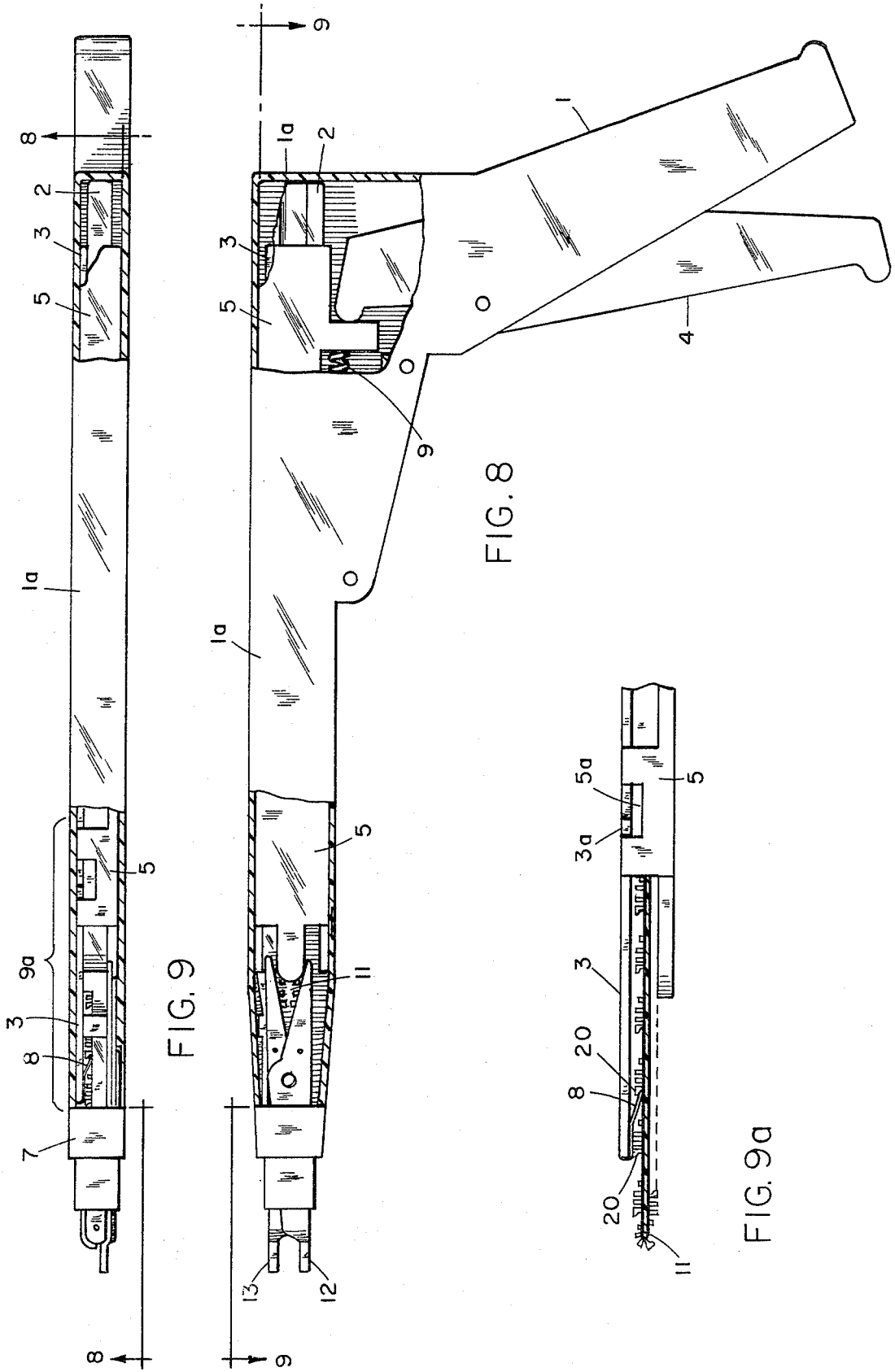

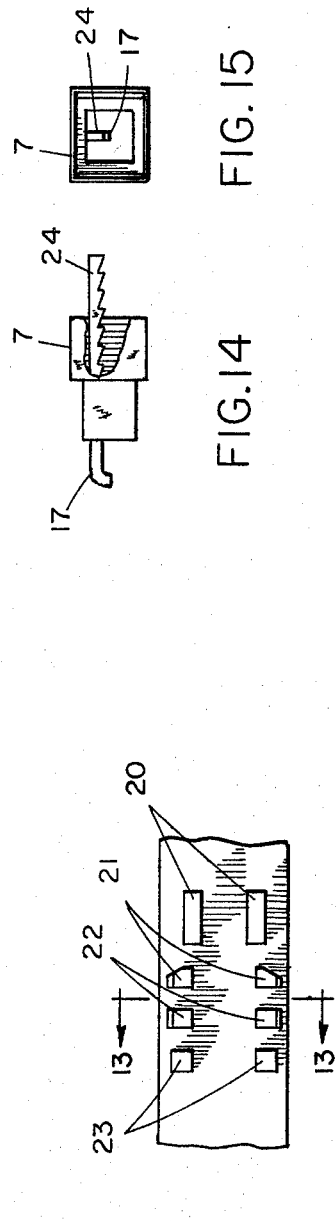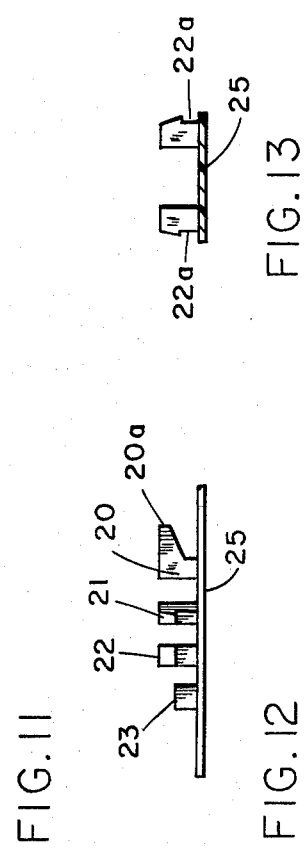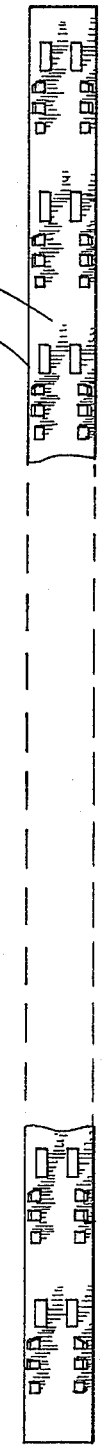

4,246,903

SURGICAL INSTRUMENT TO APPLY A HEMOSTATIC CLIP TO A VESSEL AND METHOD OF USING THE SAME

BACKGROUND AND SUMMARY OF THE INVENTION

This invention relates to a surgical instrument to apply a single hemostatic clip to a blood vessel or other internal tubular member. This invention also relates to a magazine tape containing a plurality of hemostatic clips which is contained in the surgical instrument. Finally, this invention relates to a method for applying a single hemostatic clip to a vessel or tubular member using the surgical instrument.

The Applicant is not aware of any prior art which in his judgment as a person having ordinary skill in the art anticipates or renders obvious the surgical instrument, magazine tape and method of this invention. However, to fully develop the background of the invention and to establish the state of the prior art, the following references are disclosed:

U.S. Pat. Nos. 3,837,555; and 3,650,453; and 3,086,208 teach the single injection of a surgical staple from a plurality of staples into disunited skin or fascia. In U.S. Pat. Nos. 3,837,555 and 3,650,453 the staples are contained in a flexible belt. The belt and the staples are contained in a cartridge which is adapted to be mounted on a powering instrument. The powering instrument has a power means, e.g. gas, which is used to develop rectilinear thrust against a piston. When the cartridge is mounted on the instrument, the piston thrust injects the staples into skin or fascia. Activation of the power means also causes the flexible belt to advance the next staple. U.S. Pat. No. 3,086,208 describes a manually operated skin clip applicator. A separate mechanical operation is necessary to advance the clips in the clip carrier, and to apply a single clip to skin or fascia.

A hemostatic clip applier marketed under the name Autostat ® by Axiom Medical Inc., California, U.S.A. provides a plurality of clips in a cartridge. The cartridge is contained in the applier which is manually operated by a scissors handle. One of the scissor arms requires a cocking action to deliver the next clip into the jaws.

The surgical instrument described in this invention has advantages over the prior art. In a continuous advancement and retraction motion of a trigger pivotally mounted to a handle, the jaws of the surgical instrument compress the clip on the vessel, and then receive and maintain the next clip. The weight, size and mechanical advantage of the instrument is such that it can be manually held and continuously operated with one hand. The time between hemostasis can thus be reduced and the surgeon's other hand is available for other uses, e.g., locating and/or orienting a vessel which requires hemostasis.

The jaws of the instrument are offset to give the surgeon better vision in applying the clip to the vessel. In another advantage, as compared to single loading hemostatic clip applicators, the risk of improperly loading a clip and/or dropping the clip into a patient during a surgical operation or procedure is greatly reduced. In still another advantage, the jaws do not compress the hemostatic clip until the trigger is squeezed about two-thirds of its total motion. This differential allows for accidental squeezing of the surgical instrument by the surgeon or nurse without compressing the clip.

Another advantage is the clip positioning and feeding tabs on the magazine tape which maintain the hemostatic clip in the proper position in the jaws. Still another advantage is the magazine tape which prevents a dual delivery of clips into the jaws. Finally, the length of the magazine tape in relation to the length of the barrel is such that the end of the tape becomes visible at the proximal end of the barrel when the last clip is delivered to the jaws. This allows for a visual notification of the last hemostatic clip on the tape.

The surgical instrument of this invention applies a single hemostatic clip to a vessel. The instrument comprises a housing having a barrel and a handle. Jaws are attached to the distal end of the barrel to receive and maintain a hemostatic clip. Jaw cams are attached to the proximal end of the jaws. When not actuated, spring means hold the jaws in separation.

A jaw wedge is mounted adjacent to one side of the barrel. The distal end of the wedge has a rounded leading member and a slot. The proximal end of the wedge is adjacent to the proximal end of the barrel.

A feed bar is mounted adjacent to the opposite side of the barrel. The distal end of the bar has feed pawls and tabs. The proximal end of the bar is adjacent to the proximal end of the barrel.

A tape guide is attached to the barrel between the wedge and the bar. Each side of the guide contains a longitudinal recess. The distal end of the guide is adjacent to the jaws. The proximal end is adjacent to the barrel. A freely turning roller is attached to the distal end of the guide.

A magazine tape is integrally contained in the tape guide longitudinal recess adjacent to the jaw wedge. The initial end of the tape is wrapped around the tape guide roller and is contained by the feed pawls in the tape guide longitudinal recess adjacent to the feed bar. The tap contains a plurality of hemostatic clips.

A barrel end cover is adjacent to the distal end of the guide. The end cover contains a J-shaped leading member which protrudes over the roller, and a guiderail. The guiderail is adjacent to the distal end of the feed bar.

A trigger is pivotally mounted to the handle. When not actuated, spring means hold the trigger in separation from the handle. On completely squeezing the trigger, the rounded jaw wedge leading member advances into the jaw cams. The jaws are joined and the clip is compressed. On releasing the trigger, the jaws are opened. The jaw wedge slot then coordinates with the feed bar tab to advance the tape one pitch and deliver the next clip in the tape to the jaws.

In a preferred embodiment, the inside radius of the J-shaped leading member on the end cover is approximately equal to the radius of the roller plus the thickness of the magazine tape belt. In a more preferred embodiment, the guiderail contained on the end cover has sawtooth serrations adjacent the magazine tape.

In another preferred embodiment, the jaws are channelled to receive and maintain the sides of the hemostatic clip in the jaws. In a more preferred embodiment, the distal end of the jaws are flanged to maintain the leading edges of the clip in the jaws. In a most preferred embodiment, the surgical instrument contains a magazine tape having feeding and positioning tabs which are adjacent to the apex of the clip and maintain the clip in the proper position for ligating in the jaws.

In yet another preferred embodiment, the jaw wedge leading member advances into the jaw cams after the trigger is squeezed about two-thirds of its total motion. In a more preferred embodiment, the jaw wedge slot on retraction coordinates with the feed bar tab to advance the tape one pitch, after the trigger is released about one-third of its total motion.

In a final preferred embodiment, the proximal end of the barrel has an opening to receive the initial end of the tape.

The magazine tape of this invention contains a plurality of hemostatic clips. The magazine tape comprises a flat flexible belt. A plurality of units are attached to the belt. Each unit contains a hemostatic clip. Each unit consists of in succession in parallel aligned pair of:
 leading tabs;
 side retaining tabs and apex retaining tabs;
 and feeding and positioning tabs.

The retaining tabs contain a groove adjacent to the sides of the belt. The groove has a height about equal to the thickness of a hemostatic clip. The groove has a thickness about equal to or less than the width of one side of a hemostatic clip. The portion of the apex tabs, which is adjacent to the apex of the clip, is contoured to accomodate the clip apex contour.

The feeding and positioning tabs have flanged upper portions. The flange is parallel with the longitudinal direction of the flat belt and extends away from the apex retaining tabs. The flange decreases in thickness away from the feeding and positioning tabs.

Each unit contains the leading ends of a hemostatic clip on the leading tabs and the sides and apex of a clip on the retaining tabs.

In a preferred embodiment, the thickness of the groove in the retaining tabs is contained inward from the side of the belt. In another embodiment, the flexible belt is composed of a polymeric material, e.g., polyurethane or polyethylene; or a laminated polymeric material. The laminated material can contain, e.g., paper and/or metal foil. In another preferred embodiment, the portion of the apex tabs adjacent to the clip apex is contoured to accomodate a V-shaped or a U-shaped clip apex. In still another preferred embodiment, the plurality of units is about equal to or less than 25.

The method of this invention comprises applying a single hemostatic clip to a vessel. The surgical instrument, and the preferred and more preferred embodiments of the surgical instrument described above are within the scope of this method. The method comprises:
 inserting the surgical instrument described above into a body opening;
 placing the jaws around a vessel; and
 squeezing the trigger, whereby the jaws are joined and the clip is compressed.

In a preferred embodiment, the method comprises the additional step: releasing the trigger, whereby the jaws open and then the magazine tape is advanced one pitch so that the next clip in the tape is delivered to the jaws.

BRIEF DESCRIPTION OF THE DRAWINGS

FIG. 1 is a partially broken side cross-sectional alont the line 1—1 of FIG. 2 showing the surgical instrument in the rest position;

FIG. 2 is a top cross-sectional view along the line 2—2 of FIG. 1;

FIG. 2a is a perspective view of the distal end of the surgical instrument of FIGS. 1 and 2;

FIGS. 4, 6 and 8 are partially broken side views along the lines 4—4; 6—6; and 8—8 of FIGS. 5, 7 and 9, respectively, showing the actuating mechanism of FIG. 3 in partial, and in full advancement and in partial retraction, respectively;

FIGS. 5, 7 and 9 are top views alont the lines 5—5; 7—7; and 9—9, respectively, of FIGS. 4, 6 and 8, respectively;

FIGS. 5a, 7a and 9a are partially expanded views of FIGS. 5, 7 and 9, respectively;

FIG. 10 is a partially broken front view of the surgical magazine tape;

FIGS. 11 and 12 are partially broken and expanded front and side views, respectively, of FIG. 10;

FIG. 13 is a cross-sectional view along the line 13—13 of FIG. 11;

FIG. 14 is a partially broken top view of the end cover of FIG. 2 showing the J-shaped leading member and guiderail;

FIG. 15 is a proximal end view of FIG. 14.

DESCRIPTION OF THE PREFERRED EMBODIMENT

Figure 3:
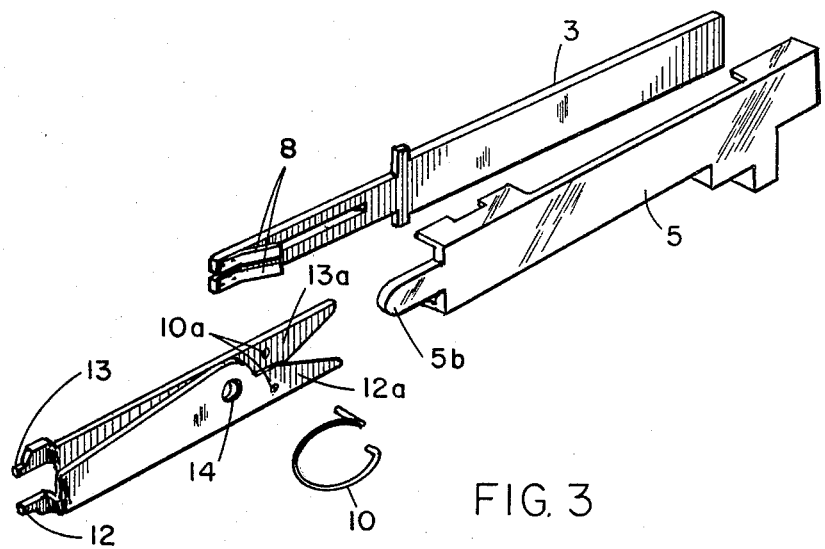
FIG. 3 is an exploded view of the jaw actuating mechanism.

In FIGS. 1 to 3, the housing 1 comprises a barrel 1a and a handle 1b. Trigger 4 is pivotally mounted to the handle by rivet 18a. In the rest position, the trigger is held open by spring 9. Tape guide 2 is attached to the barrel by rivets 18b. The tape guide 2 contains on opposite sides longitudinal recesses. One longitudinal recess is used to advance the loaded magazine tape to deliver a clip to the jaws. The other longitudinal recess is used to receive the empty magazine tape. The magazine tape (shown in FIG. 10) is pulled in the receiving longitudinal recess by feed pawls 8 located on the feed bar 3. The feed pawls operate on the tape during retraction of the jaw wedge 5, after the jaws 12 and 13 are opened. The mechanical relationship of the feed bar to the jaw wedge is described more fully in FIGS. 4 to 9a, infra.

Feed bar 3, jaw wedge 5, and jaw cams 12a and 13a are the actuating mechanism for jaws 12 and 13. The jaws and jaw cams are attached to the barrel by rivet 14 (as shown in FIG. 1). In one embodiment, the jaws are channelled to receive and maintain the sides of the hemostatic clip. In another embodiment, the distal end of the jaws are flanged to maintain the leading edges of the clip. In still another embodiment, the magazine tape has feeding and positioning tabs which are adequate to the apex of the clip and maintain the clip in the proper position for ligating in the jaws.

The jaw cams operate in a "scissors action" when engaged by the rounded jaw wedge leading member 5b. When not engaged the jaws and jaw cams are held open by torsion spring 10 inserted into holes 10a. Barrel clip 6 and end cover 7 (as shown in FIG. 1) ensure a secure fit at the distal end of the barrel 1a when the instrument is being used.

The magazine tape 11 (shown in more detail in FIGS. 10 to 13) contains a plurality of hemostatic clips. The magazine tape is loaded into the tape guide longitudinal recess adjacent the jaw wedge 5.

The configuration of the clip is not critical to the use of the surgical instrument of this invention providing: the clip can be compressed by actuation of the jaws and the next clip in the magazine tape can be delivered to the jaws. A clip having a generally U-shaped configuration can be used. The apex of the clip can have a uniform radius, or can have a rectangular or other symmetrical cross-section. The clip can be manufactured from a metallic material, e.g. tantalum, or from a polymeric material, e.g. polyglycolic acid. The inside of the clip contains friction means, e.g. serrations or diagonal slits, to prevent the compressed clip from slipping off the vessel.

The tape guide is located in the barrel 1b between the feed bar 3 and jaw wedge 5 (which are shown, in detail in FIG. 3). A sufficient lead of tape is needed to go through the end cover 7, between the roller 16 and the J-shaped leading member 17 (shown in FIGS. 2a and 14), and after turning 180°, back into the end cover and into the opposite tape guide recess. The feed pawls 8 engage the clip feeding and positioning tabs (shown, e.g., in FIG. 9a) at the initial end of the tape. The roller 16, shown in FIGS. 2a, is attached to the distal end of the tape guide by roller shaft 15. The roller 16 is used as a bearing surface for the magazine tape 11.

In FIGS. 4 to 5a squeezing the trigger 4 causes the jaw wedge 5 to advance. The jaw wedge advances about one-third of its total motion before engaging the feed bar 3. The jaw wedge then engages and moves the feed bar in the same direction for about another one-third of its total motion before engaging the jaw cams 12a and 13a. This one-third differential is caused by the jaw wedge slot 5a, which is longer than the feed bar tab 3a. When the trigger is released, the differential allows the jaws 12 and 13 to open before the next clip is delivered.

In FIGS. 6 to 7a, the final approximately one-third motion of the jaw wedge 5 causes the rounded jaw wedge leading member 5b to contact the jaw cams 12a and 13a and to close the jaws 12 and 13.

In a preferred embodiment, the total motion of the jaw wedge is about ⅜". The final approximately ¼" motion causes the jaws 12 and 13 to be "cammed" closed. The clip held between them is thus crimped. The jaws 12 and 13 completely close when the trigger 4 is fully squeezed.

In FIGS. 4 to 7a the advancement of the feed bar 3 does not cause the magazine tap 11 to feed a clip into the jaws 12 and 13 because the feed pawls 8 only engage the clip positioning and feeding tabs 20 (shown in detail in FIG. 12) on the magazine tape when the feed bar is retracting.

In FIGS. 8 to 9a, when the pressure on the trigger 4 is released, the jaw wedge 5 and trigger retract to and are held in their rest positions by spring 9. During about the first one-third of the total motion of the jaw wedge retraction, the jaws 12 and 13 open. No delivery of a clip from the magazine tape 11 occurs during this first one-third motion because the jaw wedge slot 5a is longer than and therefore does not engage the feed bar tab 3a. After about the first one-third motion, the jaw wedge slot 5a engages the feed bar tab 3a. During the final approximately two-thirds of the total motion of the jaw wedge retraction, the feed pawls 8 engage the clip positioning and feed tab 20 on magazine tape 11 and advance the tape one pitch. This causes the next clip to be delivered and inserted into the jaws 12 and 13. The jaw wedge and feed bar are stopped in their retraction by the proximal end of the barrel 1a. The feed bar 3 maintains the rest position by the spring motion of the feed pawls 8 against the magazine tape 11, by the static friction of the feed pawls against the magazine tape, and by the sawtooth guiderail 24 (shown in FIGS. 14 and 15) contained in the end cover 7.

In a preferred embodiment, the number of clips remaining in the magazine tape 11 can be visually identified. This can be done e.g., by having the tape protrude through the proximal end of the barrel 1a when a designated number of clips remain in the magazine tape.

In FIG. 10, the magazine tape 11 comprises a flat flexible belt 25. A plurality of units are attached to the belt. Each unit contains a hemostatic clip. In FIGS. 11 and 12, each unit consists of, in succession, a parallel aligned pair of: leading tabs; side retaining tabs 22 and apex retaining tabs 21; and feeding and positioning tabs 20.

In FIG. 13, the side retaining tabs 22 contain a groove 22a adjacent to the sides of the belt 25. The height and width of the groove on the apex retaining tabs 21 is identical to the groove 22a of FIG. 13. The groove 22a has a height about equal to the thickness of a hemostatic clip. The groove has a thickness about equal to or less than the width of one side of a hemostatic clip.

In FIGS. 11 and 12, the portion of the apex tabs 21 adjacent to the apex of the clip is contoured to accomodate the clip apex contour. The contour shown is for a hemostatic clip with a V-shaped apex. In FIG. 12, the feeding and positioning tabs 20 have flanged upper portions 20a. The flanged portions are parallel with the longitudinal direction of the belt 25 and extend away from the apex retaining tabs. The flanged portions are to accomodate the feed pawls 8 on the feed bar 3 (shown in FIG. 9a). The flanged portions decrease in thickness away from the feeding and positioning tabs.

In FIGS. 14 and 15, the relationship of the J-shaped leading member 17 and the guiderail 24 to the end cover 7 is described. The relationship of the end cover 7 to the barrel 1a is described in FIG. 2a.

I claim:
1. A surgical instrument to apply a single hemostatic clip to a vessel comprising:
   a housing having a barrel and a handle;
   jaws attached to the distal end of said barrel containing means to receive and maintain a hemostatic clip;
   jaw cams attached to the proximal end of said jaws;
   spring means to hold said jaws in separation;
   a jaw wedge mounted adjacent to one side of said barrel, the distal end of said wedge having a rounded leading member and a slot, and the proximal end of said wedge adjacent to the proximal end of said barrel;
   a feed bar mounted adjacent to the opposite side of said barrel, the distal end of said bar having feed pawls and tabs, and the proximal end of said bar adjacent to the proximal end of said barrel;
   a tape guide attached to said barrel between said wedge and said bar, each side containing longitudinal recess, the distal end of said guide adjacent to said jaws and the proximal end adjacent to the proximal end of said barrel;
   a freely turning roller attached to the distal end of said guide;
   a magazine tape integrally contained in the said tape guide longitudinal recess adjacent said jaw wedge, the initial end of said tape wrapped around said roller and contained by said feed pawls in said tape guide longitudinal recess adjacent said feed bar, said tape containing a plurality of hemostatic clips;
   an end cover adjacent to the distal end of said guide, containing a J-shaped leading member which protrudes over said roller, and a guiderail adjacent to the distal end of said feed bar;
   a trigger pivotally mounted to said handle;

spring means to hold said trigger in separation from said handle;

whereby on completely squeezing said trigger, said rounded jaw wedge leading member advances into said jaw cams, said jaws are joined and said clip is compressed;

and on releasing said trigger, said jaws are open and then said jaw wedge slot coordinates with said feed bar tab to advance said tape one pitch so that the next clip in said tape is delivered to said jaws.

2. A surgical instrument of claim 1 wherein the inside radius of the J-shaped leading member on said end cover is approximately equal to the radius of said roller plus the thickness of the magazine tape belt.

3. A surgical instrument of claim 2 wherein the guiderail said end cover has sawtooth serrations adjacent said tape.

4. A surgical instrument of claim 1 wherein said jaws are channeled to receive and maintain the sides of said clip in said jaws.

5. A surgical instrument of claim 4 wherein the proximal end of said barrel has an opening to receive the initial end of said tape.

6. A surgical instrument of claim 1 wherein the distal end of said jaws are flanged to maintain the leading edges of said clip in said jaws.

7. A surgical instrument of claims 4 or 6 wherein the magazine tape has feeding and position tabs, which are adjacent to the apex of the clip and maintain the said clip in the proper position in said jaws.

8. A surgical instrument of claim 6 wherein said jaw wedge slot coordinates with said feed bar tab to advance said tape one pitch after said trigger is released about one-third of its total motion.

9. A surgical instrument of claim 1 wherein said jaw wedge leading member advances into said jaw cams after said trigger is squeezed about two-thirds of its total motion.

10. A method of applying a single hemostatic clip to a vessel which comprises
    inserting the surgical instrument of claim 1 into a body opening;
    placing said jaws around a vessel; and
    squeezing said trigger, whereby said jaws are joined and said clip is compressed.

11. A method of claim 10 comprising the additional step:
    releasing said trigger, whereby said jaws open and then said tape is advanced one pitch so that the next clip in said tape is delivered to said jaws.

* * * * *